United States Patent
Hoffman et al.

(10) Patent No.: US 10,748,108 B2
(45) Date of Patent: Aug. 18, 2020

(54) MANUAL STATION SYSTEMS AND METHODS

(71) Applicant: Express Scripts Strategic Development, Inc., St. Louis, MO (US)

(72) Inventors: Robert E. Hoffman, Linden, IN (US); Jonathan W. Joplin, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 101 days.

(21) Appl. No.: 16/182,566

(22) Filed: Nov. 6, 2018

(65) Prior Publication Data

US 2019/0073625 A1    Mar. 7, 2019

Related U.S. Application Data

(63) Continuation of application No. 15/358,326, filed on Nov. 22, 2016, now Pat. No. 10,163,068.

(51) Int. Cl.
| | | |
|---|---|---|
| *G06Q 10/08* | (2012.01) | |
| *G06F 19/00* | (2018.01) | |
| *B65G 43/08* | (2006.01) | |
| *B65G 47/44* | (2006.01) | |
| *B65G 47/42* | (2006.01) | |
| *B65G 11/20* | (2006.01) | |
| *G16H 20/13* | (2018.01) | |
| *B65G 1/137* | (2006.01) | |

(52) U.S. Cl.
CPC ......... *G06Q 10/083* (2013.01); *B65G 11/203* (2013.01); *B65G 43/08* (2013.01); *B65G 47/42* (2013.01); *B65G 47/44* (2013.01); *G06F 19/3462* (2013.01); *G16H 20/13* (2018.01); *B65G 1/1378* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,337,919 A | * | 8/1994 | Spaulding | B65G 1/1373 221/127 |
| 5,720,154 A | | 2/1998 | Lasher et al. | |
| 5,771,657 A | * | 6/1998 | Lasher | B65B 61/20 53/55 |
| 5,782,339 A | * | 7/1998 | Drewitz | B65G 21/2072 198/836.3 |
| 5,943,841 A | * | 8/1999 | Wunscher | B65G 1/1376 53/154 |
| 7,185,477 B2 | | 3/2007 | Rice et al. | |
| 7,765,776 B1 | | 8/2010 | Leu et al. | |

(Continued)

*Primary Examiner* — Kyle O Logan

(57) ABSTRACT

A pharmaceutical filling system for a high volume pharmacy is described. The system can include a manual pick/pack device and method. The system may include a rotation assembly, a left door and a right door, both positioned below the rotation assembly, a left divider positioned below the left door, and a right divider positioned below the right door, and a left gathering table positioned below the left divider, and a right gathering table positioned below the right divider. The system may also include a control device in electronic communication with the rotation assembly, the doors and the dividers for control of same.

15 Claims, 10 Drawing Sheets

(56) References Cited

U.S. PATENT DOCUMENTS

| | | | |
|---|---|---|---|
| 7,912,582 B1* | 3/2011 | Holtje | G07F 11/165 |
| | | | 221/126 |
| 8,600,903 B2 | 12/2013 | Eller | |
| 9,394,107 B1 | 7/2016 | Eller et al. | |
| 9,536,369 B2* | 1/2017 | Wagner | A61G 12/001 |
| 2003/0050731 A1* | 3/2003 | Rosenblum | G16H 20/10 |
| | | | 700/232 |
| 2004/0065053 A1* | 4/2004 | Rice | B65B 5/103 |
| | | | 53/445 |
| 2004/0088187 A1* | 5/2004 | Chudy | G06Q 10/10 |
| | | | 705/2 |
| 2005/0171813 A1* | 8/2005 | Jordan | G06Q 50/22 |
| | | | 705/2 |
| 2008/0195246 A1* | 8/2008 | Tribble | G06Q 10/10 |
| | | | 700/216 |
| 2009/0173779 A1* | 7/2009 | Szesko | G06F 19/3462 |
| | | | 235/375 |
| 2012/0245728 A1* | 9/2012 | Koholka | B65G 1/1378 |
| | | | 700/216 |
| 2013/0018503 A1 | 1/2013 | Carson et al. | |
| 2013/0239524 A1 | 9/2013 | Stoetzner | |
| 2013/0246229 A1* | 9/2013 | Mountz | G06Q 10/087 |
| | | | 705/28 |
| 2014/0021253 A1* | 1/2014 | Carson | G06Q 30/018 |
| | | | 235/381 |
| 2015/0378345 A1 | 12/2015 | Winkler | |
| 2016/0137433 A1* | 5/2016 | Tempany | B65G 57/10 |
| | | | 414/789.5 |
| 2016/0229633 A1* | 8/2016 | Yamashita | B65G 1/1373 |

* cited by examiner

US 10,748,108 B2

MANUAL STATION SYSTEMS AND METHODS

CROSS-REFERENCE TO RELATED APPLICATIONS

This application is a continuation application of U.S. patent application Ser. No. 15/358,326 filed on Nov. 22, 2016, the entire disclosure of which is incorporated herein by reference.

FIELD

The present disclosure relates generally to the technical field of automated filling centers. In a specific example, the present disclosure may relate to a high volume fulfillment center (e.g., a high volume pharmacy, etc.) and to systems and methods for manual pick and manual pack station, which may include manual station.

BACKGROUND

A pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

BRIEF DESCRIPTION OF THE DRAWINGS

In the drawings, reference numbers may be reused to identify similar and/or identical elements.

DETAILED DESCRIPTION

Figure 1:
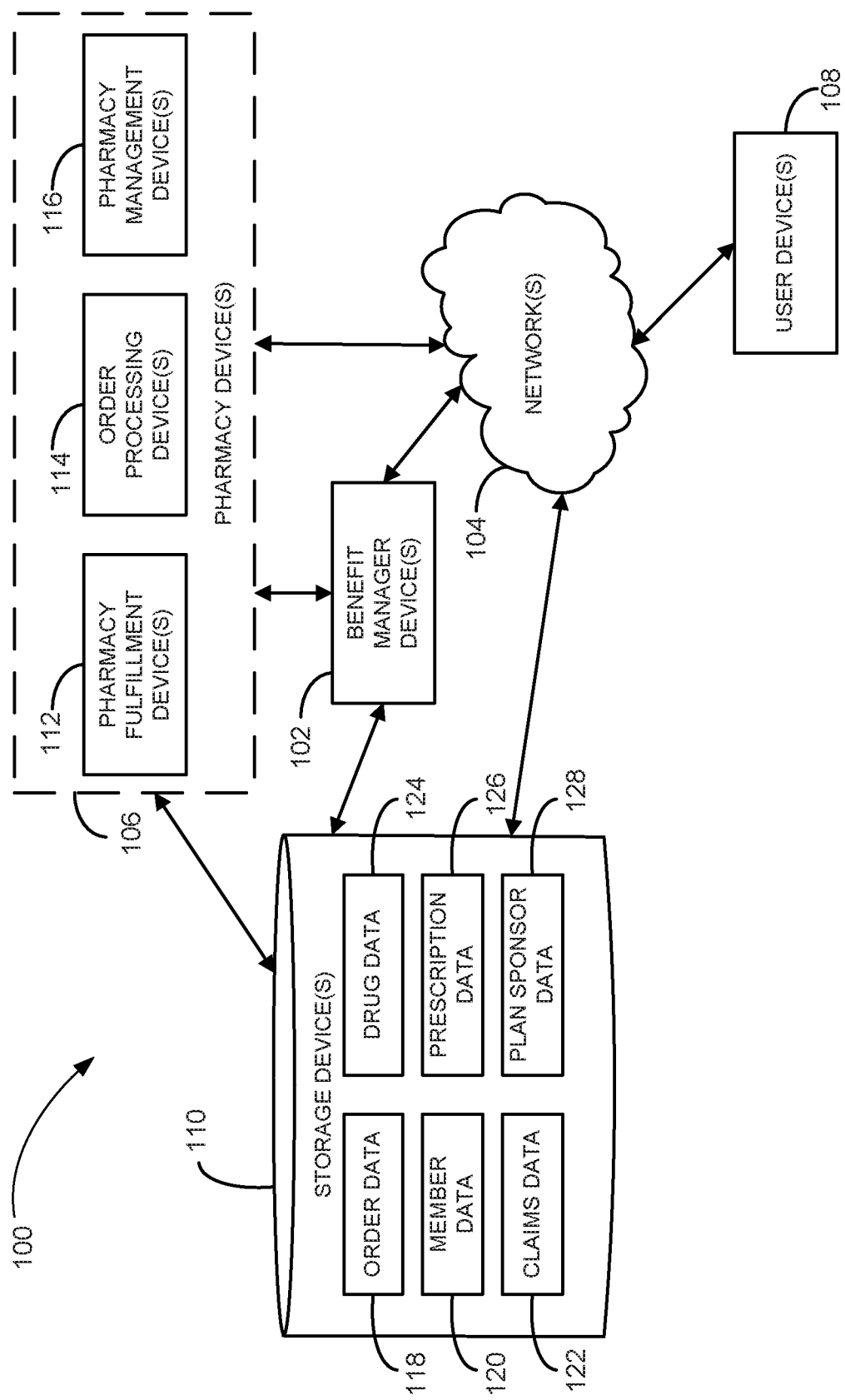
FIG. 1 is a diagram of an example implementation of a system for a high volume pharmacy, according to an example embodiment.

Example systems and methods for manual picking and manual packing, for example, in a pharmacy, are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a high volume pharmacy. The prescription order may include more than one prescription drug for fulfillment. Each prescription drug in a prescription order is an order component of the prescription order. Generally, the order components include pill bottles, liquid bottles, blister packs, unit-of-use packs, injectable package, spray bottles, tubes, ampoules, drop counters, insulated boxes, child-resistant containers, or other packaging having a quantity of a prescription drug contained therein.

In an example embodiment, a system may include a housing having an upper portion with an inner passageway and a lower portion with at least two passageways. A rotation assembly may be provided for engagement with an elevated tote to selectively rotate the elevated tote. The rotation assembly may be positioned proximate the upper portion of the housing and may be configured to rotate the elevated tote to release contents carried by the elevated tote into the inner passageway of the housing. The system may also include at least one door positioned within the housing between the upper portion and the lower portion of the housing, and at least one actuator associated with each of the at least one door. The at least one actuator may selectively open the at least one door to allow passage from the inner passageway to one of the at least two passageways. The system may further include at least one slide positioned within each of the at least two passageways beneath the at least one door, and at least one gathering table positioned at a bottom of each slide.

In an example embodiment, a system may include a rotation assembly, and a left door and a right door, both positioned below the rotation assembly. A left divider may be positioned below the left door, and a right divider may be positioned below the right door. A left gathering table may be positioned below the left divider, and a right gathering table may be positioned below the right divider. A control device may also be provided in electronic communication with the rotation assembly, the doors and the dividers. The control device may be operable to rotate the rotation assembly upon detecting the absence of an object positioned above the left and right doors; open the left door upon detecting the absence of an object above the left divider; open the right door upon detecting the absence of an object above the right divider; open the left divider upon detecting the absence of an object on the left gathering table; and open the right divider upon detecting the absence of an object on the right gathering table.

In an example embodiment, a method may sensing the presence or absence of an object positioned within an inner passageway of an upper portion of a housing, causing a rotation assembly to rotate a tote upon detecting the absence of an object within the inner passageway, thereby causing contents of the tote to fall into the inner passageway of the upper portion of the housing, sensing the presence or absence of an object positioned above a left divider or a right divider, actuating a left door upon detecting the absence of an object above the left divider, thereby causing an object previously held back by the left door to fall to the left divider; actuating a right door upon detecting the absence of an object above the right divider, thereby causing an object previously held back by the right door to fall to the right divider; sensing the presence or absence of an object on a left gathering table or a right gathering table; actuating the left divider upon detecting the absence of an object on the left gathering table, thereby causing an object previously held back by the left divider to fall onto a left slide to the left gathering table; and actuating the right divider upon detecting the absence of an object on the right gathering table, thereby causing an object previously held back by the right divider to fall onto a right slide to the right gathering table.

The prescription drugs may be dispensed at various sections of the high volume pharmacy. Some prescription orders may require manual handling of certain order components. Some prescription order components may be filled automatically by filling machinery.

Distribution of order components necessitating manual handling is provided by a distribution section and one or more than one manual sections. In general, manual handling includes manual fulfillment of prescription drugs. Manual handling occurs at one or more than one manual sections, and may utilize a manual fulfillment device. Some prescription orders may be filled using automated machines, which can fill prescription orders at a greater rate than manual fulfillment.

FIG. 1 is a block diagram of an example implementation of a system 100, according to an example embodiment. While the system 100 is generally described as being deployed in a high volume pharmacy or fulfillment center (e.g., a mail order pharmacy, a direct delivery pharmacy, an automated pharmacy, multiple package delivery center, and the like), the system 100 and/or components thereof may otherwise be deployed (e.g., in a lower volume pharmacy). A high volume pharmacy may be a pharmacy that is capable of filling prescriptions automatically, mechanically, manually, or a combination thereof. The system 100 may include a benefit manager device 102, a pharmacy device 106, and a user device 108, which may communicate with each other directly and/or over a network 104. The system 100 may also include a storage device 110.

The benefit manager device 102 is a device operated by an entity that is at least partially responsible for creation and/or management of the pharmacy or drug benefit. While such an entity operating the benefit manager device 102 is typically a pharmacy benefit manager (PBM), other entities may operate the benefit manager device 102 either on behalf of themselves, the PBM, another entity, or other entities. For example, the benefit manager device 102 may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, specialty pharmacies, pharmaceutical vending machines or kiosks, and the like.

Some of the operations of the PBM that operates the benefit manager device 102 may include the following activities and processes. A member (or a person on behalf of the member) of a pharmacy benefit plan administered by or through the PBM attempts to obtain a prescription drug at a retail pharmacy location (e.g., a location of a physical store) from a pharmacist or a pharmacist technician. The member may also attempt to obtain the prescription drug through mail order drug delivery from a mail order pharmacy location, which may be the high volume pharmacy system 100. In some embodiments, the member may also attempt to obtain the prescription drug directly or indirectly through the use of a machine, such as a kiosk, vending unit, mobile electronic device, or a different type of mechanical, electrical, electronic communication device, and/or computing device. Such a machine may be filled with the prescription drug in prescription packaging, which may include multiple prescription components, by the high volume pharmacy system 100.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, or the like. In some instances, an employer of the member may directly or indirectly fund or reimburse the member for the copayments.

The amount of the co-pay required from the member may vary with different pharmacy benefit plans having different plan sponsors or clients and/or prescription drugs. The member's copayment may be based a flat copayment (e.g., $10 or other dollar amounts), coinsurance (e.g., 10% or other percents), and/or a deductible (e.g., for first $500 of annual prescription drug expenses or other dollar amounts) for certain prescription drugs, certain types and/or classes of prescription drugs, and/or all prescription drugs. The copayment may be stored in the storage 110 or determined by the benefit manager device 102.

In some instances, the member may not pay the copayment or may only pay a portion of the copayment for the prescription drug. For example, if the usual and customary cost for a generic version of a prescription drug is $4, and the member's flat copayment is $20 for the prescription drug, the member may only be required to pay $4 to receive the prescription drug. In another example involving a worker's compensation claim, no copayment may be due by the member for the prescription drug.

In addition, copayments may also vary based on different delivery channels used for the prescription drug to be received by the member. For example, the copayment for receiving the prescription drug from a mail order pharmacy location may be less than the copayment for receiving the prescription drug from a retail pharmacy location.

In conjunction with receiving the copayment (if any) from the member and dispensing the prescription drug to the member, the pharmacy submits a claim to the PBM for the prescription drug. After receiving the PBM (e.g., through the benefit manager device 102) may perform certain adjudication operations including verifying eligibility for the member, identifying and/or reviewing an applicable formulary for the member to determine any appropriate copayment, coinsurance, and deductible for the prescription drug, and performing a drug utilization review (DUR) on the member. The PBM provides a response to the pharmacy (e.g. from the benefit manager device 102 to the pharmacy device 106) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on the type(s) of pharmacy network in which the pharmacy is included. Other factors may also be used to determine the amount in addition to the type of pharmacy network. For example, if the member pays the pharmacy for the prescription drug without using the prescription drug benefit provided by the PBM (e.g., by paying cash without use of the prescription drug benefit or by use of a so-called pharmacy discount card offering other negotiated rates), the amount of money paid by the member may be different than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored on the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include an optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102, 106-110 or in parallel to link the devices 102, 106-110.

The pharmacy device 106 may include an order processing device 114, a pharmacy management device 116, and a pharmacy fulfillment device 112 in communication with each other directly and/or over the network 104.

The order processing device 114 may receive information regarding filling prescriptions and may direct an order component to one or more than one of the devices of the pharmacy fulfillment device 112 at a pharmacy. The pharmacy fulfillment device 112 may fulfill, dispense, aggregate, and/or pack the order components of the prescription drugs in accordance with one or more than one of the prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the pharmacy fulfillment device 112. In some embodiments, the order processing device 114 may be an external device separate from the pharmacy and communicate with other devices located within the pharmacy.

For example, the external order processing device 114 may communicate with an internal order processing device 114 and/or other devices located within the system 100. In some embodiments, the external order processing device 114 may have limited functionality (e.g., as operated by a patient requesting fulfillment of a prescription drug), while the internal pharmacy order processing device 114 may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together.

The pharmacy management device 116 may enable and/or facilitate management and operations in a pharmacy. For example, the pharmacy management device 116 may provide functionality to enable receipt and processing of prescription drug claims, management of pharmacy personnel, management of pharmaceutical and non-pharmaceutical products, track products in the pharmacy, record workplace incidents involve personnel and products, and the like. In some embodiments, the order processing device 114 may operate in combination with the pharmacy management device 116.

In some embodiments, the pharmacy management device 116 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy management device 116 may be utilized by the pharmacy to submit the claim to the PBM (e.g., through the benefit management device 102) for adjudication.

In some embodiments, the pharmacy management device 116 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager 102 may track prescription drug fulfillment and/or other information for patients that are not members or have not identified themselves as members, at the time (or in conjunction with the time) in which they seek to have a prescription filled at a pharmacy.

The pharmacy fulfillment devices 112, the order processing device 114, and/or the pharmacy management device 116 may include circuitry, a processor, a memory to store data and instructions, and communication functionality. These devices 112-116, in some embodiments, are dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage) and/or through the network 104 (e.g., by utilizing a cloud configuration or software as a service. etc.) with the storage 110.

The user device 108 is used by a device operator. The device operator may be a user (e.g., an employee, a contractor, a benefit member, a patient of the pharmacy, or the like) associated with the system 100. Other device operators may also operate the user device 108. In some embodiments, the user device 108 may enable the device operator to attend to pharmacy operations in a convenient manner (e.g., remote from a pharmacy). In some embodiments, the user device 108 may enable the device operator to receive information about pharmacy processes, prescription drug fulfillment status, and the like.

The user device 108 may be a stand-alone device that solely provides at least some of the functionality of the methods and systems, or may be a multi-use device that has functionality outside of analysis of the methods and systems. Examples of the user device 108 include a set-top box (STB), a receiver card, a mobile telephone, a personal digital assistant (PDA), a display device, a portable gaming unit, a computing system, and the like. Other devices, however, may also be used. In some embodiments, the computing system may include a mobile computing device. For example, the user device 108 may include a mobile electronic device, such an iPhone or iPad by Apple, Inc., mobile electronic devices powered by Android by Google, Inc., and a Blackberry by Research In Motion Limited. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, and the like) in communication with the benefit manager device 102, the pharmacy device 106, and/or the user device 108 directly and/or over the network 104. The non-transitory storage may store order data 118, member 120, claims data 122, drug data 124, prescription data 126, and/or plan sponsor 128. Further, the system 100 may include additional devices, which may communicate with each other directly or over the network 104.

The order data 118 may be related to a prescription order. The order data may include the type of the prescription drug (e.g., drug name and strength) and quantity of the prescription drug. The order data 118 may also include data used for completion of the prescription, such as prescription materials and/or the type and/or size of container in which the drug is dispended or in which is requested to be dispensed. In general, prescription materials include an electronic copy of information regarding the prescription drug for inclusion with or otherwise provided (e.g., via email) in conjunction with the fulfilled prescription. The prescription materials may include electronic information regarding drug interaction warnings, recommended usage, possible side effects, expiration date, date of prescribing, or the like. The order data 118 may be used by the pharmacy to fulfill a pharmacy order.

In some embodiments, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging, and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to facilitate transportation of prescriptions within the pharmacy may also be stored as order data 118.

The member data 120 includes information regarding the members associated with the PBM. The information stored as member data 120 may include personal information, personal health information, protected health information, fitness data, health data, web and mobile app activity, and the like. Examples of the member data 120 include name, address, telephone number, e-mail address, prescription drug history, and the like. The member data 120 may include a plan sponsor identifier that identifies the plan sponsor associated with the member and/or a member identifier that identifies the member to the plan sponsor. The member data 120 may also include, by way of example, dispensation preferences such as type of label, type of cap, message preferences, language preferences, or the like.

The member data 120 may be accessed by various devices in the pharmacy to obtain information utilized for fulfillment and shipping of prescription orders. In some embodiments, an external order processing device 114 operated by or on behalf of a member may have access to at least a portion of the member data 120 for review, verification, or other purposes.

In some embodiments, the member data 120 may include information for persons who are patients of the pharmacy but are not members in a pharmacy benefit plan being provided by PBM. For example, these patients may obtain drug directly from the pharmacy, through a private label service offered by the pharmacy, or otherwise. In general, the use of the terms member (e.g., of a prescription drug benefit plan) and patient (e.g., of a pharmacy) may be used interchangeably in this disclosure.

The claims data 122 includes information regarding pharmacy claims adjudicated by the PBM under a drug benefit program provided by the PBM for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility, and the like. Additional information may be included.

In some embodiments, other types of claims beyond prescription drug claims may be stored in the claims data 122. For example, medical claims, dental claims, wellness claims, or other type of health care-related claims for members may be stored as a portion of the claims data 122.

In some embodiments, the claims data 122 includes claims that identify the members with whom the claims are associated. In some embodiments, the claims data 122 includes claims that have been de-identified (e.g., associated with a unique identifier but not with a particular, identifiable member), aggregated, and/or otherwise processed.

The drug data 124 may include drug name (e.g., technical name and/or common name), other names by which the drug is known by, active ingredients, an image of the drug (e.g., in pill form), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, and the like.

Figure 2:
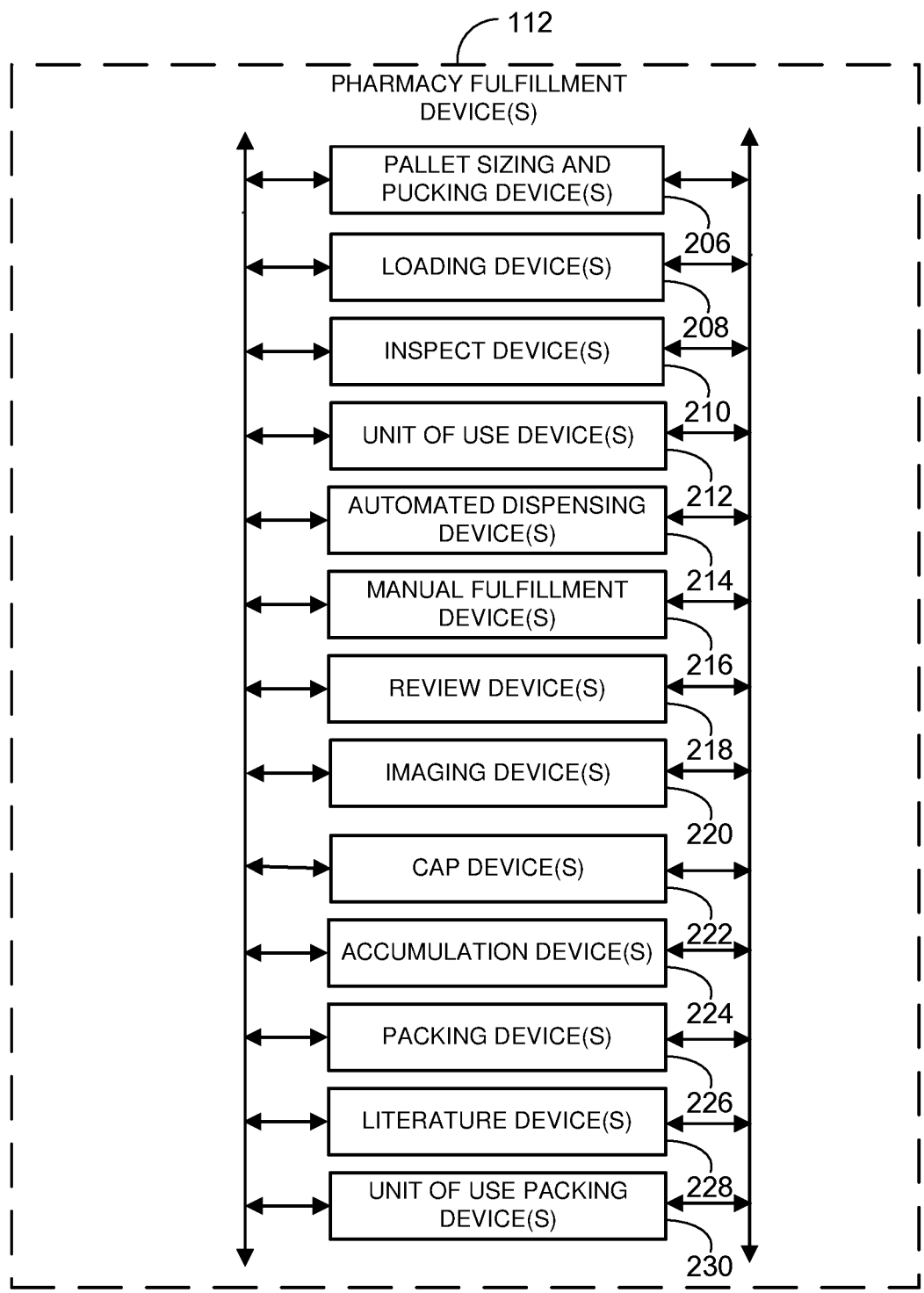
FIG. 2 is a block diagram of an example pharmacy fulfillment devices that may be deployed within the system of FIG. 1, according to an example embodiment.

FIG. 2 illustrates the pharmacy fulfillment device 112, according to an example embodiment. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the non-transitory storage 110, directly or over the network 104. Specifically, the pharmacy fulfillment device 112 may include pallet sizing and pucking device(s) 206; loading device(s) 208; inspect device(s) 210, unit of use device(s) 212, automated dispensing device(s) 214, manual fulfillment device(s) 214, review device(s) 218, imaging device(s) 220, cap device(s) 222, accumulation device(s) 224, literature device(s) 228, packing device(s) 226, and unit of use packing device(s) 230. Further, the pharmacy fulfillment device 112 may include additional devices, which may communicate with each other directly or over the network.

In some embodiments, operations performed by one or more of these devices 206-230 may be performed sequentially, or in parallel with the operations of other devices as may be coordinated by the order processing device 114. In some embodiments, the order processing device 114 tracks a prescription with the pharmacy based on operations performed by one or more than one of the devices 206-230.

In some embodiments, the pharmacy fulfillment device 112 may transport prescription drug containers, for example, between more than one of the devices 206-230 in the high volume fulfillment center, by use of pallets. The pallet sizing and pucking device 206 may configure pucks in a pallet. A pallet may be a transport structure for a number of prescription containers, and may include a number of cavities. A puck may be placed in one or more than one the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism, or the like. In one embodiment, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations, (e.g., at the high volume fulfillment center, or the like).

The inspect device 210 may verify that containers in a pallet are correctly labeled and in the correct spot on the pallet. The inspect device 210 may scan the label on one or more than one containers on the pallet. Labels of containers may be scanned or imaged in full or in part by the inspect device 210. Such imaging may occur after the container has been lifted out of its puck by a robotic arm, picker, or the like, or may be otherwise scanned or imaged while retained in the puck. In some embodiments, images and/or video captured by the inspect device 210 may be stored in the storage device 110 as a portion of the order data 118.

The unit of use device 212 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, liquids in a spray or other dispensing container, and the like. Prescription drug products dispensed by the unit of use device 212 may be packaged individually or collectively for shipping, or may be shipped in combination with other prescription drugs dispensed by other devices (e.g., in the high volume fulfillment center).

At least some of the operations of devices 206-230 may be directed by the order processing device 114. For example, the manual fulfillment device 216, the review device 218, the automated dispensing device 214, the packing device 226, and/or another device may receive instructions provided by the order processing device 114.

The automated dispensing device 214 may include one or more than one devices that dispenses prescription drugs or pharmaceuticals into prescription containers in accordance with one or multiple prescription orders. In general, the automated dispensing device 214 may include mechanical and electronic components with, in some embodiments, software and/or logic to facilitate pharmaceutical dispensing that would otherwise be performed in a manual fashion by a pharmacist and/or pharmacist technician. For example, the automated dispensing device 214 may include high volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high volume fulfillment center.

The manual fulfillment device 216 may provide for manual fulfillment of prescriptions. For example, the manual fulfillment device 216 may receive or obtain a container and enable fulfillment of the container by a pharmacist or pharmacy technician. In some embodiments, the manual fulfillment device 216 provides the filled container to another device in the pharmacy fulfillment devices 112 to be joined with other containers in a prescription order for a patient or member. In general, a manual fulfillment may include operations at least partially performed by a pharmacist or a pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 216 may be packaged individually or collectively for shipping, or may be shipped in combination with other prescription drugs dispensed by other devices in the high volume fulfillment center.

The review device 218 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review may be performed at the manual station.

The imaging device 220 may image containers prior to filling and/or after they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114, and/or stored in the storage device 110 as part of the order data 118.

The cap device 222 may be used to cap or otherwise seal a prescription container. In some embodiments, the cap device 222 may secure a prescription container with a type of cap in accordance with a patient preference (e.g., a preference regarding child resistance, a preference regarding built-in adherence functionality, or the like), a plan sponsor preference, a prescriber preference, or the like. The cap device 222 may also etch a message into the cap, although this process may be performed by a different device in the high volume fulfillment center. The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218, at the high volume fulfillment center. The accumulation device 224 may be used to group the prescription containers prior to shipment to the member or otherwise.

The literature device 228 prints, or otherwise generates, literature to include with prescription drug orders. The literature may be printed on multiple sheets of substrates, such as paper, coated paper, printable polymers, or combinations thereof. The literature printed by the literature device 228 may include information required to accompany the prescription drugs included in a prescription order, relating to prescription drugs in the order, financial information associated with the order (e.g., an invoice or an account statement, or the like).

In some embodiments, the literature device 228 folds or otherwise prepares the literature for inclusion with a prescription drug order (e.g., in a shipping container). In some embodiments, the literature device 228 that prints the literature may be separate from the literature device that prepares the literature for inclusion with a prescription order.

The packing device 226 packages a prescription order in preparation for shipping the order. The packing device 226 may box, bag, or otherwise package the fulfilled prescription order for delivery. The packing device 226 may further place inserts, (e.g., literature or other papers), into the packaging received from the literature device 228 or otherwise. For example, bulk prescription orders may be shipped in a box, while other prescription orders may be shipped in a bag which may be a wrap seal bag. The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, sort by zip code, or the like). The packing device 226 may include ice or temperature sensitive elements for prescriptions which are to be kept within a temperature range during shipping in order to retain efficacy or otherwise. The ultimate package may then be shipped through postal mail, through a mail order delivery service that ships via ground and/or air (e.g., UPS, FEDEX, DHL, or the like), through delivery service, through a locker box at a shipping site (e.g., AMAZON locker, a PO Box, or the like), or otherwise.

The unit of use packing device 230 packages a unit of use prescription order in preparation for shipping the order. The unit of use packing device 230 may include manual scanning of containers to be bagged for shipping to verify each container in the order. In an example embodiment, the manual scanning may be performed at a manual station.

While the pharmacy fulfillment device 112 in FIG. 2 is shown to include single devices 206-230, multiple devices may be used. The devices 206-230 may be the same type or model of device or may be different device types or models. When multiple devices are present, the multiple devices may be of the same device type or models or may be a different device type or model. The types of devices 206-230 shown in FIG. 2 are example devices. In other configurations of the system 100, lesser, additional, or different types of devices may be included.

Moreover, multiple devices may share processing and/or memory resources. The devices 206-230 may be located in the same area or in different locations. For example, the devices 206-230 may be located in a building or set of adjoining buildings. The devices 206-230 may be interconnected (e.g. by conveyors), networked, and/or otherwise in contact with one another or integrated with one another, (e.g., at the high volume fulfillment center). In addition, the functionality of a device may be split among a number of discrete devices and/or combined with other devices.

Figure 3:
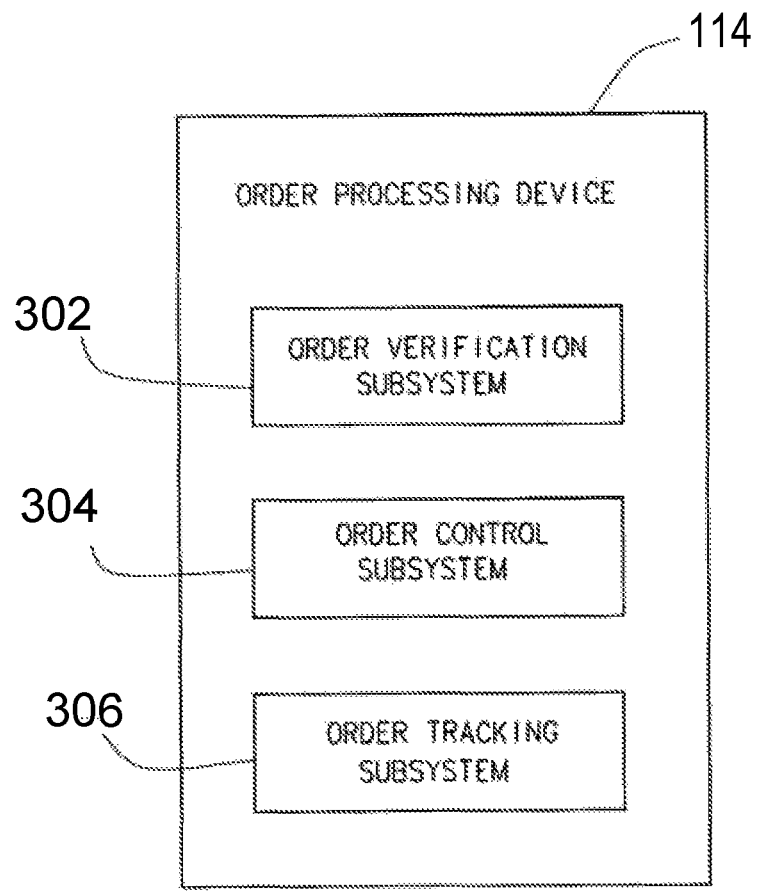
FIG. 3 is a block diagram of an example order processing device that may be deployed within the system of FIG. 1, according to an example embodiment.

FIG. 3 illustrates the order processing device 114, according to an example embodiment. The order processing device 114 may be used by one or more than one operators to generate prescription orders, make routing decisions, make prescription order consolidation decisions, track literature with the system 100, and/or view order status and other order related information. For example, the prescription order may consist of order components. The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to, verify the eligibility of the member, and review the formulary to determine appropriate copayment, coinsurance, and deductible for the prescription drug, and/or perform a DUR. Other communications between the order verification subsystem 302 and the benefit manager device 102 may be performed for a variety of purposes.

The order control subsystem 304 controls various movements of the containers and/or pallets along with various filling functions during their progression through the system 100. In some embodiments, the order control subsystem 304 may identify the prescribed drug in one or more than one prescription orders as capable of being fulfilled by the automated dispensing device 214. The order control subsystem 304 may determine which prescriptions are to be launched, and may determine that a pallet of automated-fill containers is to be launched. The order control subsystem 304 may determine that an automated-fill prescription of a specific pharmaceutical is to be launched, and may examine a queue of orders awaiting fulfillment for other prescription orders which will be filled with the same pharmaceutical. The order control subsystem 304 may then launch orders with similar automated-fill pharmaceutical needs together in a pallet to the automated dispensing device 214. As the devices 206-230 may be interconnected by a system of conveyors or other container movement systems, the order control subsystem 304 may control various conveyors to deliver the pallet from the loading device 208 to the manual fulfillment device 216, for example, from the literature device 228 to deliver paperwork as needed to fill the prescription.

The order tracking subsystem 306 may track a prescription order as it progresses (or stops) toward fulfillment. The order tracking subsystem 306 may track, record and/or update order history, order status, or the like. The order tracking subsystem 306 may store data locally (e.g., in a memory, etc.) or as a portion of the order data 118 stored in the storage 110.

Figure 4:
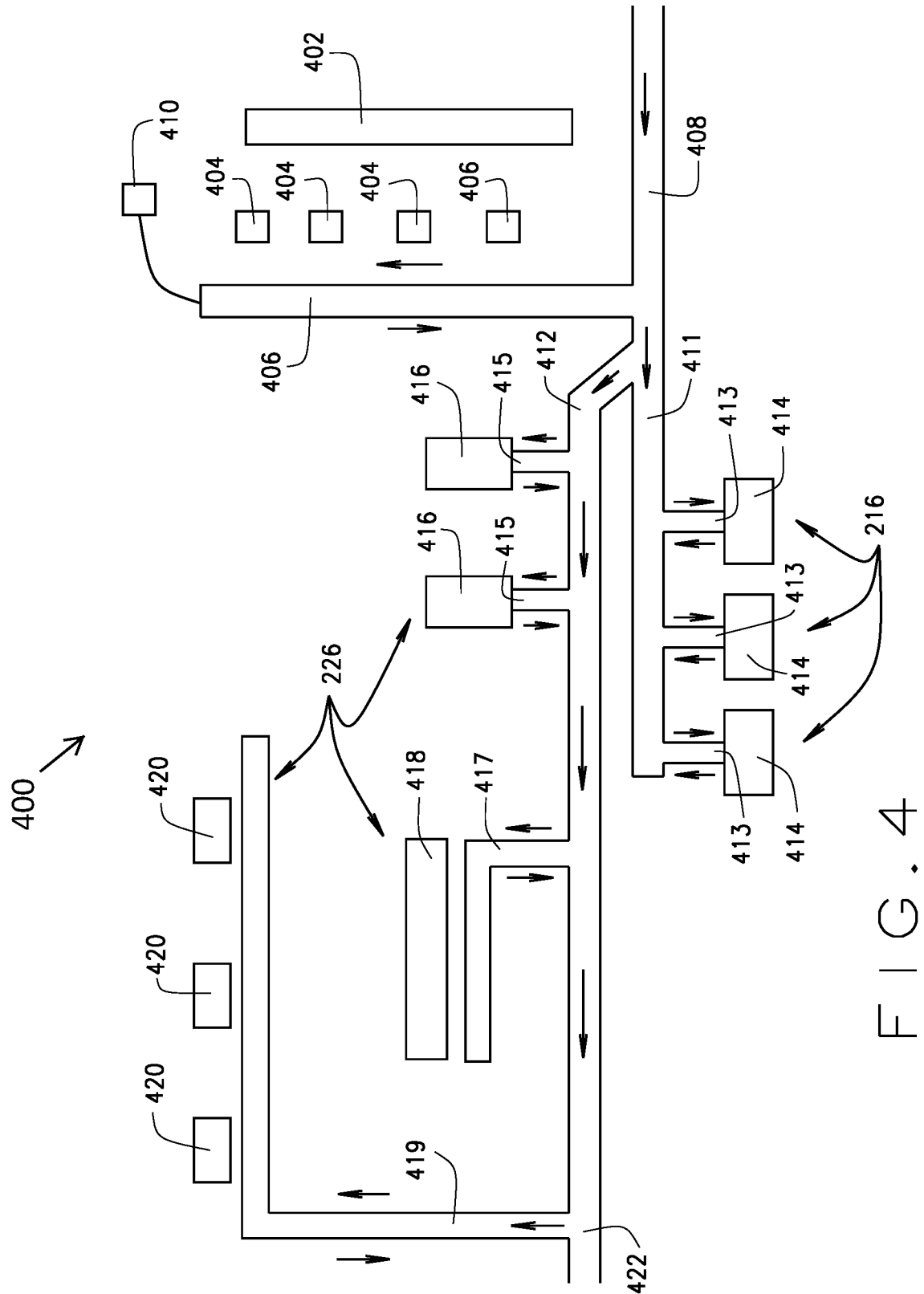
FIG. 4 is a block diagram of a portion of the example system of FIG. 1, according to an example embodiment.

FIG. 4 illustrates a block diagram of a portion 400 of the system 100, according to an example embodiment, which may include manual fulfillment device(s) 216 and packing device(s) 226. As shown in FIG. 4, a reach-in cooler 402 is associated with one or more than one ice pick stations 404. A prescription order may include a pharmaceutical that is to be kept cool, such that it is held in a reach-in cooler or other refrigerated storage. The prescription order that includes this type of pharmaceutical may be packaged with a coolant of some type for shipping, and therefore may be considered as an ice order. Orders filled at an ice pick station 404 from the reach-in cooler 402 leave the ice pick stations 404 via a conveyor 406, which may feed onto a conveyor 408 coming from other devices within the system 100, such as the automated dispensing device 214. The conveyors 406, 408, or any other conveyor discussed herein may consist of multiple separate conveyors, and may be unidirectional or bidirectional, such as via multi-level conveyors. Such conveyors may therefore be waist-level conveyors or elevated conveyors or both. Totes may be used to contain prescription components while in route on a conveyor. A control unit 410, which may be deployed within the order processing device 114 in an embodiment, may control one or more than one of the conveyors and routing of various prescription orders or components of prescription orders through the system 100.

After coming from the ice pick station 404, an ice order may be sent from the conveyor 408 to the conveyor 411 toward the manual fulfillment device 216. Ice orders may be routed to the manual fulfillment device 216 if the ice order includes another prescription component that needs to be filled at the manual fulfillment device 216. The manual fulfillment device 216 may include one or more manual pick stations 414. A tote may be carried to a manual pick station 414 from the conveyor 411 by a conveyor 413, which may be fed from the conveyor 411. When the ice order from the ice pick station 404 arrives at the manual pick station 414, a worker may fill one or more than one additional components of the prescription order with one or more than one pharmaceuticals at the manual pick station 414. The worker may thereby marry the one or more than one newly filled prescription order components with any associated ice order components from the ice pick station 404. A tote containing the married prescription order may exit the manual fulfillment device 216 via the conveyors 411 and 413. Such an order may still be considered the ice order, due to the presence of a pharmaceutical that is to be shipped with a coolant.

When a prescription order is completed at the ice pick station 404, or when a prescription order is completed at the manual pick station 414, it may proceed to a conveyor 412 and then to the packing device 226. The packing device 226 may be a manual pack station 416, a wrap seal device 418, and/or an ice pack station 420. Ice orders that will fit within a wrap seal pocket may be routed to the wrap seal device 418 to be packaged via a conveyor 417. Ice orders that are too large to be packaged by the wrap seal device 418 may be routed instead to the manual pack station 416 via conveyor 415. A worker at the manual pack station 416 may manually pack the ice order.

In either case, once packaged, such orders may be routed to the ice pack station 420 via a conveyor 419. Ice orders may then proceed to other parts of the system 100 for continued processing and preparation for shipment.

Figure 5:
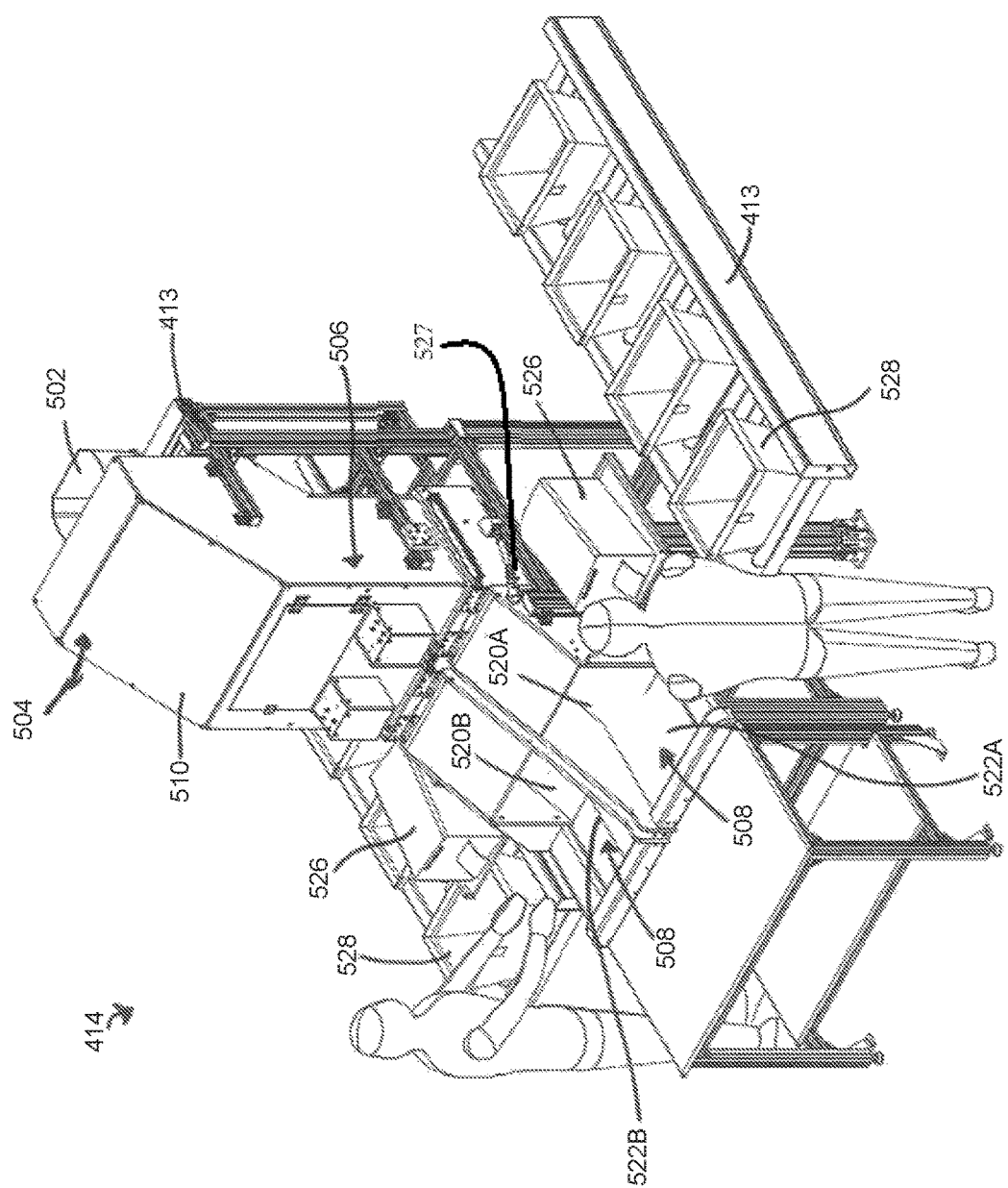
FIG. 5 is a perspective view of a an example manual pick station, according to an example embodiment.
Figure 6:
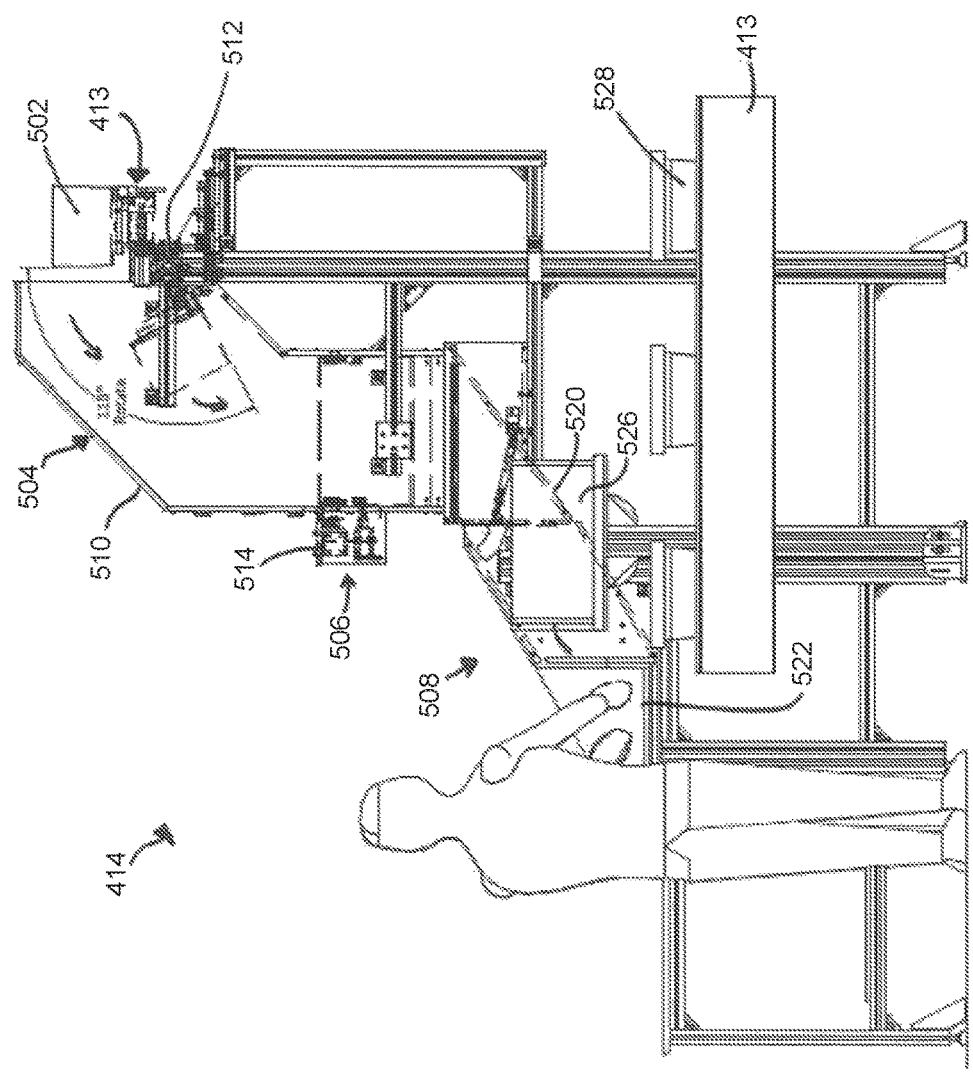
FIG. 6 is a side elevation view of the manual pick station of FIG. 5, according to an example embodiment.
Figure 7:
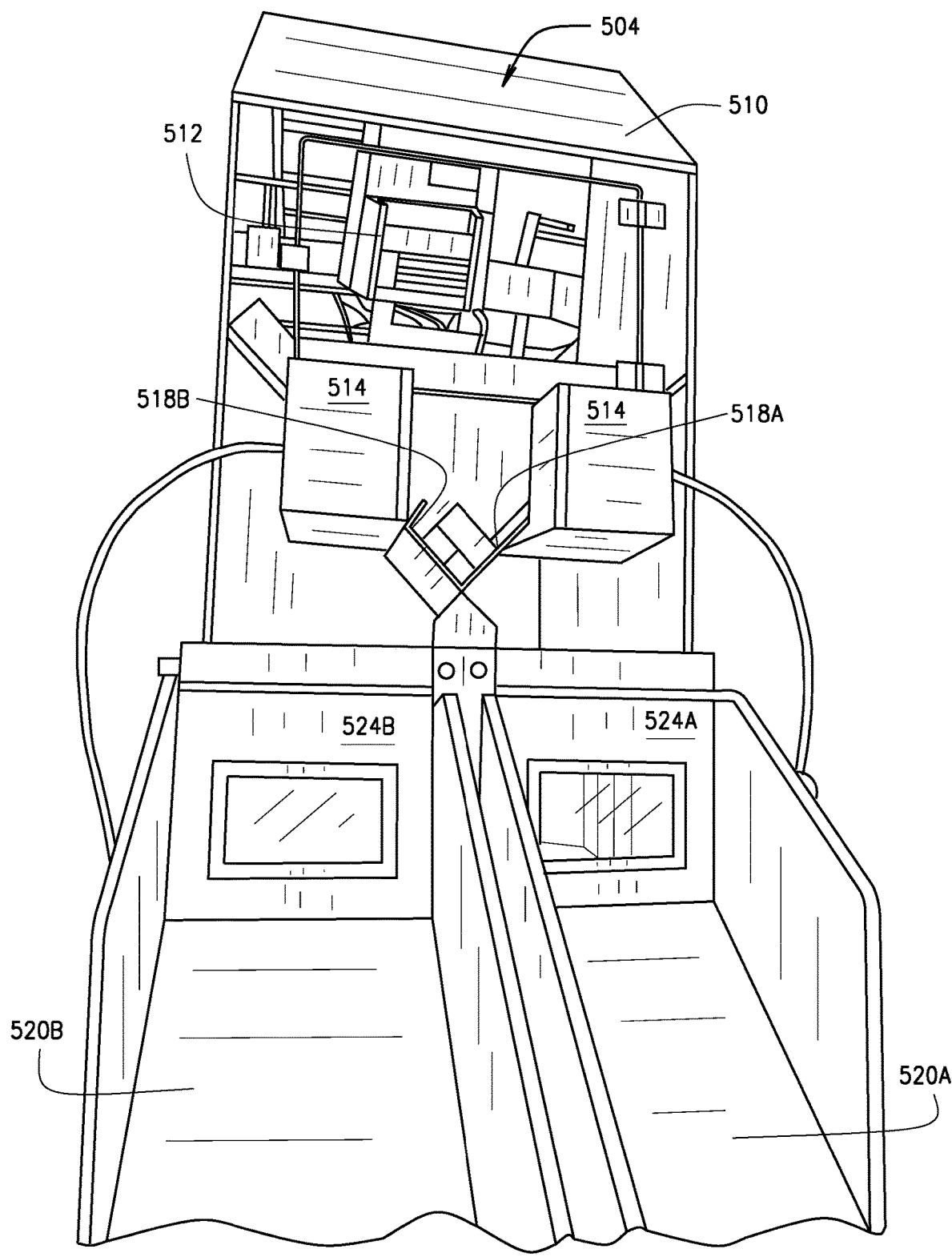
FIG. 7 is a front elevation view of the manual pick station of FIGS. 5 and 6, according to an example embodiment.

FIGS. 5-7 show an example embodiment of the manual pick station 414. It will be understood that the manual pack station 416 may have a similar structure as the manual pick station 414 in FIGS. 5-7. A partial ice order, or other partial order, may arrive at the manual pick station 414 in a tote 502 on the elevated inflow conveyor 413, as best seen in FIGS. 5 and 6. The manual pick station 414 may include a rotator stage 504, an actuator stage 506, and a gathering stage 508. The tote 502 may arrive proximate the rotator stage 504. As shown in FIGS. 5 and 6, the tote 502 may be rotated into a housing 510 by a rotation assembly 512, thereby dumping the contents of the tote 502 into the housing 510, toward the actuator stage 506.

At the actuator stage 506, an actuator 514 may be associated with and positioned to move a door 518. In an example embodiment, an actuator 514 may be a 45-degree actuator or a linear actuator. The example embodiment in FIG. 7 includes a right door 518A and a left door 518B, each of which is associated with a respective actuator 514. When actuated, the right door 518A may allow prescription order components to pass onto a right slide 520A and to a right table 522A. When actuated, the left door 518B may allow prescription order components to pass onto the left slide 520B and to a left table 522B of the gathering stage 508. Right and left moveable dividers 524A and 524B, which may be actuated by additional actuators 527, may prevent order components from passing down the right and the left slides 520A, 520B, respectively, to allow for staging of orders. In an example embodiment, an actuator 527 may be approximately a 30-degree angle actuator. Once on the left table 522B or the right table 522A, a worker may perform any desired action. For example, a worker may scan a component on the table 522 to determine which additional pharmaceuticals may be associated with that order, and may fill such additional prescription component. Thereby, any components on the table 522 may be married with additional order components filled by the worker at the manual pick station 414. The worker may label the newly filled order component(s) with a label from a printer 526, and may then marry all of the order components in a tote 528 on the outflow conveyor 413. As shown in FIGS. 5 and 6, the outflow conveyor 413 may be at waist level, which may in some embodiments be at a different level than the inflow conveyor 413.

As mentioned above, FIGS. 5, 6, and 7 have been discussed in terms of the manual pick station 414. However, the manual pack station 416 may have substantially the same structure. When a prescription order arrives on the table 522 of the manual pack station 416, a worker may pack the one or more than one components of the prescription order manually.

Figure 8:
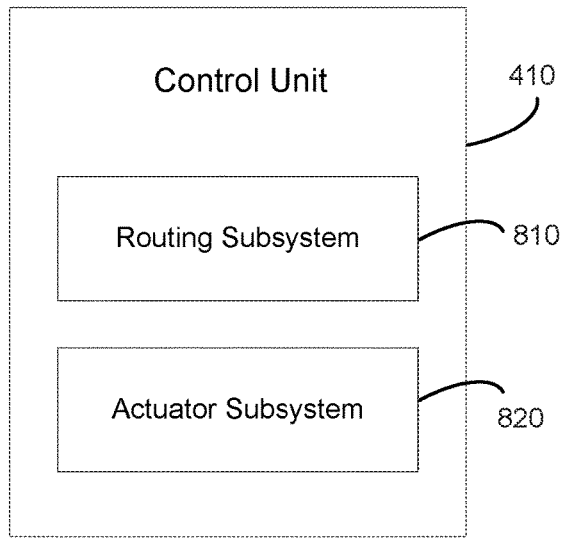
FIG. 8 is a block diagram of an example control unit of a manual pick station, according to an example embodiment.

FIG. 8 illustrates the control unit 410, according to an example embodiment. The control unit 410 may be deployed in the portion 400, or may otherwise be deployed.

The control unit 410 may include a routing subsystem 810 and an actuator subsystem 820. Each subsystem may include circuitry, e.g., processors, logic, and memory, to execute instructions on sensed data. The control unit 410 may be responsible, as a non-limiting example, for directing prescription ice orders to various devices in the system 100. For example, the control unit 410 may be communicatively coupled to the stations 414, 416, the actuators 514, the assemblies 512, and the like. The routing subsystem 810 may enable the control unit 410 to direct prescription orders and/or partial prescription orders to various devices within the system 100, and may communicate with various stations and/or workers at those stations. The actuator subsystem 820 may control various actuators and assemblies, including the actuators 514 and the rotation assembly 512.

Figure 9:
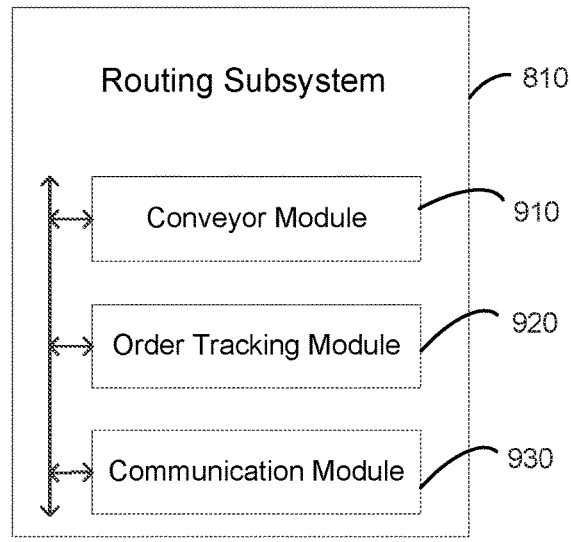
FIG. 9 is a block diagram of an example routing subsystem of a manual pick station, according to an example embodiment.

FIG. 9 illustrates an example routing subsystem 810 that may be deployed in the control unit 410, or may be otherwise deployed in another system. One or more than one modules are communicatively coupled and included in the routing subsystem 810 to enable the routing subsystem 810 to control flow prescription orders within the system 100. The modules of the routing subsystem 810 that may be included are a conveyor module 910, an order tracking module 920, and a communication module 930. Other modules may also be included. Each module may include circuitry, e.g., processors, logic, and memory, to execute instructions on sensed data or calculated data.

In some embodiments, the modules of the routing subsystem 810 may be distributed so that some of the modules are deployed in other devices within the pharmacy. In one embodiment, the modules are deployed in memory and executed by a processor coupled to the memory. The functionality contained within the modules 910-930 may be combined into a lesser number of modules, further divided among a greater number of modules, or redistributed among existing modules. Other configurations including the functionality of the modules 910-930 may be used.

The conveyor module 910 may communicate with one or more conveyors, such as the conveyors 406, 408, 411, 412, 413, 415, 417, 419, and 422 in an example embodiment. Such conveyors may be controlled by the conveyor module 910 to route prescription orders and/or partial prescription orders through the system 100 to various devices. The order tracking module 920 may track the location and status of such prescription orders and/or partial prescription orders within the system 100, thereby allowing the conveyor module 910 to properly route such orders through the system 100. Similarly, the communication module 930 may communicate with one or multiple workers at one or more than one station within the system 100, such as the manual pick station 414 and/or the manual pack station 416. A worker may scan an order component on the table 522, and the scanned information may be communicated to the control unit 410 via the communication module 930. Communication module 930 may then provide the worker with additional information regarding the prescription order with which the scanned order component is associated. For example, communication module 930 may identify additional pharmaceuticals to be filled by the worker. Such communication further allows the order tracking module 920 to track and further route prescription orders through the system 100.

Figure 10:
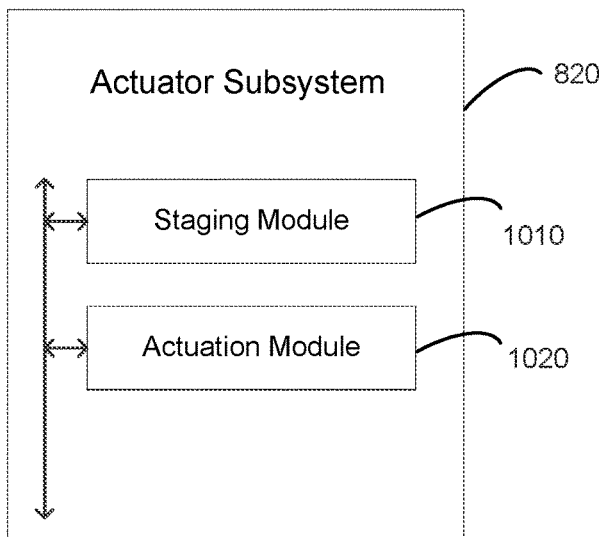
FIG. 10 is a block diagram of an example actuator subsystem of a manual pick station, according to an example embodiment.

FIG. 10 illustrates an example actuator subsystem 820 that may be deployed in the control unit 410, or may be otherwise deployed in another system. One or more than one module are communicatively coupled and included in the actuator subsystem 820. Each module may include circuitry, e.g., processors, logic, and memory, to execute instructions on sensed data or calculated data. The modules of the actuator subsystem 820 that may be included are a staging module 1010 and an actuation module 1020. Other modules may also be included.

In some embodiments, the modules of the actuator subsystem 820 may be distributed so that some of the modules are deployed in other devices within the pharmacy. In one embodiment, the modules are deployed in memory and executed by a processor coupled to the memory. The functionality contained within the modules 1010-1020 may be combined into a lesser number of modules, further divided among a greater number of modules, or redistributed among existing modules. Other configurations including the functionality of the modules 1010-1020 may be used.

The staging module 1010 may be in communication with one or more than one sensors, including but not limited to door sensors, divider sensors, and table sensors, to determine whether a prescription order is present at various locations within a station, such as the manual pick station 414 or the manual pack station 416. For example, an order may be positioned within the tote 502 at the atop inflow conveyor 413, at the closed doors 518A, 518B, behind a moveable divider 524, or on the table 522. When staging module 1010 detects that any of such locations do not contain a prescription order, the actuation module 1020 may cause actuators or assemblies to engage, thereby allowing the next order to proceed. For example, when the staging module determines that the table 522 is empty, the actuation module 1020 may cause the associated moveable divider 524 to move, thereby allowing an order waiting behind the divider 524 to advance to the table 522. Thereafter, the staging module 1010 may determine that the moveable divider 524 no longer retains a prescription order, and the actuation module 1020 may then cause the actuator 514 to open the door 518, thereby allowing an order waiting the door 518 to advance to the divider 524. Thereafter, the staging module 1010 may determine that the door 518 no longer retains a prescription order, and the actuation module 1020 may then cause rotation assembly 512 to rotate, thereby allowing an order contained in the tote 502 to drop into the housing 510 and to the doors 518A, 518B.

Figure 11:
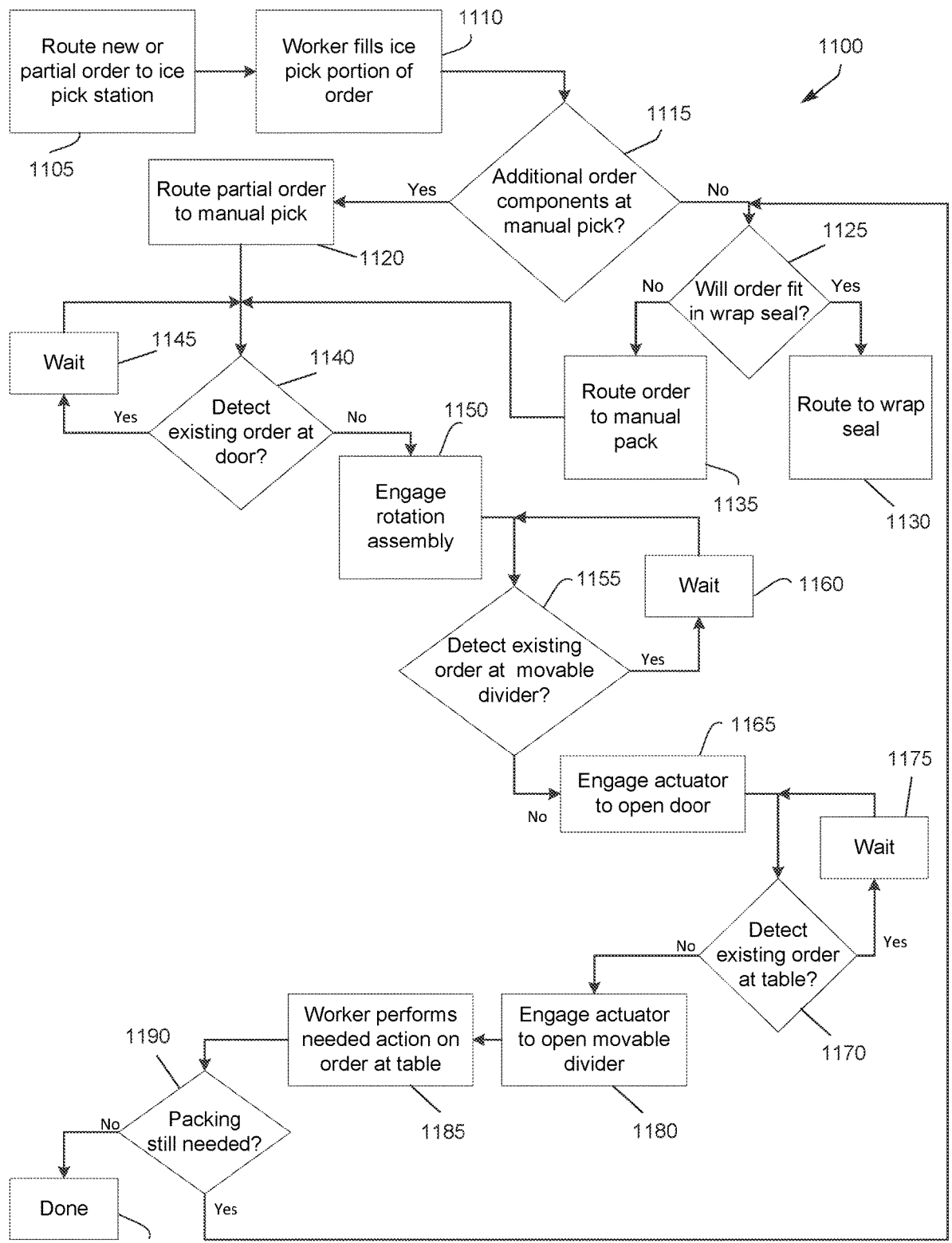
FIG. 11 is a flow diagram of an example manual pick and pack method, according to an example embodiment.

FIG. 11 illustrates a method 1100 for routing ice orders through a pharmacy, and for operating a pick/pack station as discussed above. The method 1100 may be performed by the manual pick station 414 and/or the manual pack station 416 (e.g., as instructed by control unit 410), or may be otherwise performed.

At block 1105, a new or partially filled order is routed to an ice pick station 404. At block 1110, a worker fills an ice pick portion of the order. At decision point 1115, a determination is made as to whether the order includes additional components to be fulfilled at the manual pick station 414. When the order does include additional manual pick components, at block 1120 the partial order is routed to the manual pick station 414.

However, where there are not additional components to be filled at the manual pick station 414, the method 1100 advances to decision point 1125, at which a determination is made whether the order will fit in a wrap seal package. Where the order will fit in a wrap seal package, the order is routed to the wrap seal device 418 at block 1130. However, where the order will not fit in a wrap seal package, the order is routed to a manual pack station at block 1135. Regardless of whether the order is routed to the manual pack station 416 at block 1135 or is routed to the manual pick station 414 at block 1120, the following sequence of steps remains the same.

At decision point 1140, a determination is made regarding whether there is an existing order at doors 518. Where there is an existing order at the doors 518, the method 1100 waits at block 1145, and then returns to decision point 1140. Once there is no longer an existing order at the doors 518, the method 1100 advances to block 1150 in which the rotation assembly 512 is engaged, releasing the order down to the doors 518. Next, at decision point 1155, a determination is made regarding whether there is an existing order at a moveable divider 524. Where there is an existing order at the moveable divider 524, the method 1100 waits at block 1160, and then returns to decision point 1155. Once there is no longer an existing order at the moveable divider 524, the method 1100 advances to block 1165 in which an actuator 1014 is engaged, allowing the order to pass through the door 518 to the moveable divider 524. Next, at decision point 1170, a determination is made regarding whether there is an existing order at a table 522. Where there is an existing order at the table 522, the method waits at block 1175, and then returns to decision point 1170. Once there is no longer an existing order at the table 522, the method advances to block 1180 in which an actuator is engaged, allowing the order to pass through the moveable divider 524 to the table 522.

At block 1185, a worker at the table 522 performs a desired action on the order. Where the worker is at the manual pick station 414, the worker would scan the order, determine which manual pick pharmaceutical is to be filled, and fill the manual pick pharmaceutical. The method 1100 would then advance to decision point 1190, where it would be determined that additional packing is needed. The method 1100 then reverts back to decision point 1125 for determination as to whether the order will fit in a wrap seal package. However, where the worker is at a manual pack station, the worker would manually pack the order. The method 1100 would then advance to decision point 1190, where it would be determined that no additional packing is necessary. The method 1100 then ends at block 1195. It will, however, be understood that additional steps may be taken as the order is further routed within the pharmacy. For example, the packaged order may be routed to an ice pack station or the like.

Figure 12:
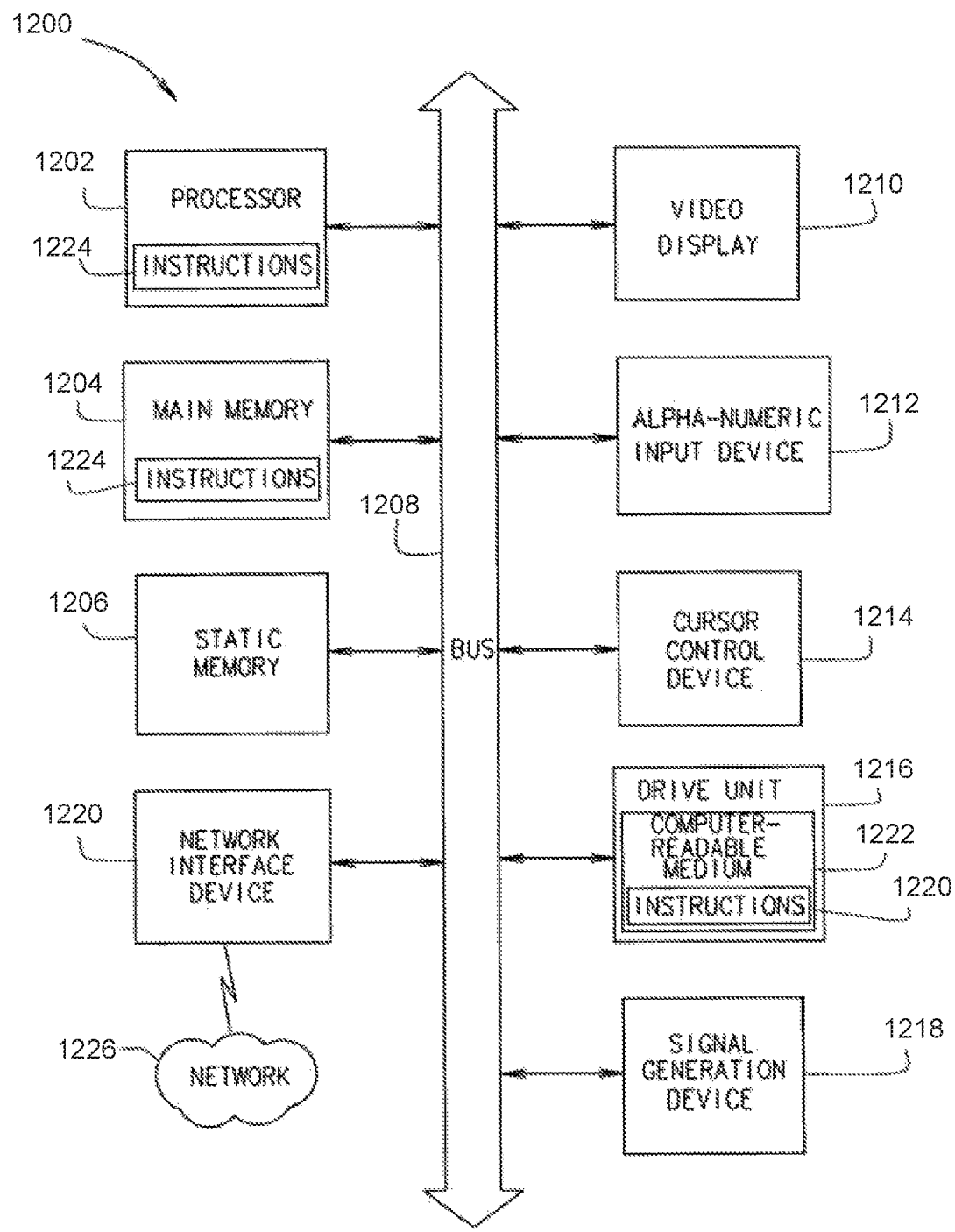
FIG. 12 is a block diagram of a machine in the example form of a computer system within which a set of processor-executable instructions for causing the machine to perform any one or more than one methodologies discussed herein may be executed or stored.

FIG. 12 shows a block diagram of a manual station in the example form of a computer system 1200 within which a set of instructions may be executed causing the machine to perform any one or more than one methods, processes, operations, or methodologies discussed herein. The devices 206-230, for example, may include the functionality of the one or more than one computer systems 1200. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 1200 includes a processor 1202 (e.g., a central processing unit (CPU), a graphics processing unit (GPU) or both, etc.), a main memory 1204 and a static memory 1206, which communicate with each other via a bus 1208. The computer system 1200 further includes a video display unit 1210 (e.g., a liquid crystal display (LCD) or a cathode ray tube (CRT), etc.). The computer system 1200 also includes an alphanumeric input device 1212 (e.g., a keyboard, etc.), a cursor control device 1214 (e.g., a mouse, etc.), a drive unit 1216, a signal generation device 1218 (e.g., a speaker, etc.) and a network interface device 1220.

The drive unit 1216 includes a computer readable medium 1222 on which is stored one or more than one sets of instructions (e.g., software 1224, etc.) embodying any one or more than one methodologies or functions described herein. The instructions 1224 may also reside, completely or at least partially, within the main memory 1204 and/or within the processor 1202 during execution thereof by the computer system 1200, the main memory 1204 and the processor 1202 also constituting non-transitory computer readable media.

When loaded with the instructions 1224, the processor 1202 is a machine dedicated to only the present processes and methodologies.

The instructions 1224 may further be transmitted or received over a network 1226 via the network interface device 1220.

While the computer-readable medium 1222 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present invention. The term "Computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and sub-systems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

The inventive subject matter may be represented in a variety of different embodiments of which there are many possible permutations.

The present disclosure makes reference to a robot and words of similar import. A robot can be a machine capable of carrying out a complex series of actions automatically. These complex series of actions may include picking up, orientating, positioning and/or releasing a prescription component, a pill, a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, may move location, have an articulated arm, have grasping structures that replicate fingers and do not damage containers, and the like.

In an example embodiment, a system may comprise a housing having an upper portion with an inner passageway and a lower portion with at least two passageways. A rotation assembly may be provided for engagement with an elevated tote to selectively rotate the elevated tote. The rotation assembly may be positioned proximate the upper portion of the housing and may be configured to rotate the elevated tote to release contents carried by the elevated tote into the inner passageway of the housing. The system may also include at least one door positioned within the housing between the upper portion and the lower portion of the housing, and at least one actuator associated with each of the at least one door. The at least one actuator may selectively open the at least one door to allow passage from the inner passageway to one of the at least two passageways. The system may further include at least one slide positioned within each of the at least two passageways beneath the at least one door, and at least one gathering table positioned at a bottom of each slide.

In an example embodiment, the at least two passageways may include at least one left inner passageway and at least one right inner passageway. The at least one slide may include a left slide positioned within the left inner passageway beneath the at least one door, and a right slide positioned within the right inner passageway beneath the at least one door. The at least one gathering table may include a left gathering table positioned at a bottom of the left slide and a right gathering table positioned at a bottom of the right slide. The at least one door may include a left door associated with the left inner passageway, and a right door associated with the right inner passageway. The at least one actuator may include two actuators, wherein one actuator is associated with the left door and one actuator is associated with the right door. The system may also include a left divider positioned in the left inner passageway above the left slide for staging objects above the left slide and left gathering table, and a right divider positioned in the right inner passageway above the right slide for staging objects above the right slide and right gathering table. An actuator associated with the left divider may move the left divider, and an actuator associated with the right divider may move the right divider. At least one door sensor device may be positioned above the doors to detect the presence or absence of an object within the inner passageway above the doors. At least one divider sensor may be associated with each divider to detect the presence or absence of an object above the respective left and right dividers. At least one table sensor may be associated with each gathering table to detect the presence or absence of an object on the respective left and right gathering tables. The left and right gathering tables may each include a scanner device for scanning pharmaceutical order components, and a printer.

A control device may be in electronic communication with the rotation assembly and the actuators, and may be operable to direct the rotation assembly to rotate a tote, thereby releasing the contents of the elevated tote into the inner passageway of the housing. The control device may further control one of the at least one actuator to open the at least one door, thereby allowing an object to pass through the at least one door into either the left or the right inner passageway. The control device may further control a first one of the actuators to open the left door, thereby directing a first object to pass through the left door into the left inner passageway, and control a second one of the actuators to open the right door, thereby directing a second object to pass through the right door into the right inner passageway. The control device may control a third one of the actuators to open the left divider, thereby directing a third object to pass through the left divider onto the left slide, and control a fourth one of the actuators to open the right divider, thereby directing a fourth object to pass through the right divider onto the right slide. The control device may further receive scan data regarding a scanned pharmaceutical order component from the scanner and determine additional pharmaceuticals order components associated with the scanned component, and instruct the printer to print information associated with the order components.

The control device may further receive sensing data from the sensors; direct the rotation assembly to rotate a tote upon detecting the absence of an object above the doors within the inner passageway based on the sensing data, thereby releasing the contents of the elevated tote into the inner passageway of the housing; control a first actuator of the actuators to open the left door upon detecting the absence of an object above the left divider based on the sensing data, thereby causing contents at the left door to pass through the left door into the left inner passageway; control a second actuator of the actuators to open the right door upon detecting the absence of an object above the right divider based on the sensing data, thereby causing contents at the right door to pass through the right door into the right inner passageway; control a third actuator of the actuators to open the left divider upon detecting the absence of an object on the left gathering table based on the sensing data, thereby causing contents at the left door to pass through the left divider onto the left slide; and cause one of the actuators to open the right divider upon detecting the absence of an object on the right gathering table based on the sensing data, thereby causing contents at the right divider to pass through the right divider onto the right slide.

In an example embodiment, a system may include a rotation assembly, and a left door and a right door, both positioned below the rotation assembly. A left divider may be positioned below the left door, and a right divider may be positioned below the right door. A left gathering table may be positioned below the left divider, and a right gathering table may be positioned below the right divider. A control device may also be provided in electronic communication with the rotation assembly, the doors and the dividers. The control device may be operable to rotate the rotation assembly upon detecting the absence of an object positioned above the left and right doors; open the left door upon detecting the absence of an object above the left divider; open the right door upon detecting the absence of an object above the right divider; open the left divider upon detecting the absence of an object on the left gathering table; and open the right divider upon detecting the absence of an object on the right gathering table.

In an example embodiment, a method may include the steps of sensing the presence or absence of an object positioned within an inner passageway of an upper portion of a housing, causing a rotation assembly to rotate a tote upon detecting the absence of an object within the inner passageway, thereby causing contents of the tote to fall into the inner passageway of the upper portion of the housing, sensing the presence or absence of an object positioned above a left divider or a right divider, actuating a left door upon detecting the absence of an object above the left divider, thereby causing an object previously held back by the left door to fall to the left divider; actuating a right door upon detecting the absence of an object above the right divider, thereby causing an object previously held back by the right door to fall to the right divider; sensing the presence or absence of an object on a left gathering table or a right gathering table; actuating the left divider upon detecting the absence of an object on the left gathering table, thereby causing an object previously held back by the left divider to fall onto a left slide to the left gathering table; and actuating the right divider upon detecting the absence of an object on the right gathering table, thereby causing an object previously held back by the right divider to fall onto a right slide to the right gathering table.

Thus, methods and systems for manual picking and manual packing have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The invention claimed is:

1. A system comprising:
   a housing having an upper portion with an inner upper passageway and a lower portion with a first lower passageway and a second lower passageway;
   a first door and a second door positioned within the housing between the upper portion and the lower portion of the housing;
   a first actuator associated with the first door, the first actuator selectively opening the first door to allow passage from the inner upper passageway to the first lower passageway;
   a second actuator associated with the second door, the second actuator selectively opening the second door to allow passage from the inner upper passageway to the second lower passageway;
   a first slide positioned within the first lower passageway beneath the first door;
   a second slide positioned within the second lower passageway beneath the second door;

a first gathering table positioned at a bottom of the first slide; and a second gathering table positioned at a bottom of the second slide.

2. The system of claim 1, further comprising:
a rotation assembly for engagement with an elevated tote to selectively rotate the elevated tote, the rotation assembly being positioned proximate the upper portion of the housing and configured to rotate the elevated tote to release contents carried by the elevated tote into the inner upper passageway of the housing.

3. The system of claim 2, further comprising:
an elevated inflow conveyor to transport the elevated tote to the rotation assembly.

4. The system of claim 2, further comprising:
a control device in electronic communication with the rotation assembly, the first actuator, and the second actuator, the control device being operable to
direct the rotation assembly to rotate the elevated tote, thereby releasing the contents of the elevated tote into the inner upper passageway of the housing, and
signal the first actuator to open the first door or the second actuator to open the second door, thereby allowing at least a portion of the contents to pass through the first door into the first lower passageway or through the second door into the second lower passageway.

5. The system of claim 2, further comprising:
a first divider positioned in the first lower passageway above the first slide for object staging above the first slide and the first gathering table;
a second divider positioned in the second lower passageway above the second slide for object staging above the second slide and the second gathering table;
a third actuator associated with the first divider for moving the first divider; and
a fourth actuator associated with the second divider for moving the second divider.

6. The system of claim 5, further comprising:
a control device in electronic communication with the rotation assembly and the actuators, wherein the control device is operable to
direct the rotation assembly to rotate a said elevated tote, thereby releasing the contents of the elevated tote into the inner upper passageway of the housing,
signal the first actuator to open the first door, thereby directing a first object to pass through the first door into the first lower passageway,
signal the second actuator to open the second door, thereby directing a second object to pass through the second door into the second lower passageway,
signal the third actuator to open the first divider, thereby directing a third object to pass through the first divider onto the first slide,
signal the fourth actuator to open the second divider, thereby directing a fourth object to pass through the second divider onto the second slide.

7. The system of claim 5, further comprising:
at least one door sensor device positioned above the doors to detect object presence or object absence within the inner upper passageway above the doors;
at least one divider sensor associated with each divider to detect object presence or object absence above the respective first and second dividers; and
at least one table sensor associated with each gathering table to detect object presence or object absence on the respective first and second gathering tables.

8. The system of claim 7, further comprising:
a control device in electronic communication with the rotation assembly and the actuators, the control device being operable to
receive sensing data from the sensors,
direct the rotation assembly to rotate a said elevated tote upon detecting object absence above the doors within the inner upper passageway based on the sensing data, thereby releasing the contents of the elevated tote into the inner upper passageway of the housing,
control the first actuator to open the first door upon detecting object absence above the first divider based on the sensing data, thereby causing contents at the first door to pass through the first door into the first lower passageway,
control the second actuator to open the second door upon detecting object absence above the second divider based on the sensing data, thereby causing contents at the second door to pass through the second door into the second lower passageway,
control the third actuator to open the first divider upon detecting object absence on the first gathering table based on the sensing data, thereby causing contents at the first divider to pass through the first divider onto the first slide, and
cause the fourth actuator to open the second divider upon detecting object absence on the second gathering table based on the sensing data, thereby causing contents at the second divider to pass through the second divider onto the second slide.

9. The system of claim 1, wherein the first door is a left door and the second door is a right door.

10. A system comprising:
a cooler to maintain temperature of associated pharmaceuticals;
an ice pick station associated with the cooler to enable fulfillment of a refrigerated pharmaceutical component of a prescription order;
a conveyor to transport the refrigerator pharmaceutical component from the ice pick station;
a manual pick station to enable fulfillment of a non-refrigerated pharmaceutical component of the prescription order, the manual pick station including a housing having an upper portion with an inner upper passageway and a lower portion with a first lower passageway and a second lower passageway, a first door and a second door positioned within the housing between the upper portion and the lower portion of the housing, a first actuator associated with the first door, the first actuator selectively opening the first door to allow passage from the inner upper passageway to the first lower passageway, a second actuator associated with the second door, the second actuator selectively opening the second door to allow passage from the inner upper passageway to the second lower passageway, a first slide positioned within the first lower passageway beneath the first door, a second slide positioned within the second lower passageway beneath the second door, a first gathering table positioned at a bottom of the first slide, and a second gathering table positioned at a bottom of the second slide; and
a packing station to enable combined packing of the refrigerated pharmaceutical component and the non-refrigerated pharmaceutical component of the prescription order.

11. The system of claim 10, further comprising:
a tote to receive the refrigerated pharmaceutical component and the non-refrigerated pharmaceutical component of the prescription order and enable transportation of a plurality of pharmaceutical components within a pharmacy.

12. The system of claim 11, further comprising:
an additional conveyor to transport the tote to the packing station,
wherein the packing station includes a manual pack station.

13. The system of claim 10, the packing station includes a wrap seal machine to package together the refrigerated pharmaceutical component and the non-refrigerated pharmaceutical component.

14. A system comprising:
a manual pick station to enable fulfillment a plurality of pharmaceutical components of a prescription order; and
a manual packing station to enable combining the plurality of pharmaceutical components of the prescription order, the manual packing station including a housing having an upper portion with an inner upper passageway and a lower portion with a first lower passageway and a second lower passageway, a first door and a second door positioned within the housing between the upper portion and the lower portion of the housing, a first actuator associated with the first door, the first actuator selectively opening the first door to allow passage from the inner upper passageway to the first lower passageway, a second actuator associated with the second door, the second actuator selectively opening the second door to allow passage from the inner upper passageway to the second lower passageway, a first slide positioned within the first lower passageway beneath the first door, a second slide positioned within the second lower passageway beneath the second door, a first gathering table positioned at a bottom of the first slide, and a second gathering table positioned at a bottom of the second slide.

15. The system of claim 14, wherein a first pharmaceutical component of the plurality of pharmaceutical components is a refrigerated pharmaceutical component and a second pharmacy component of the plurality of pharmaceutical components is a non-refrigerated pharmaceutical component.

* * * * *